United States Patent [19]

Koch et al.

[11] Patent Number: 5,437,203
[45] Date of Patent: Aug. 1, 1995

[54] SAMPLING DEVICE COMPRISING A REVOLVABLE SAMPLING WHEEL WITH A METAL WHEEL RIM

[75] Inventors: Dieter Koch, Weyhe-Leeste; Gerd Menne, Bremen; Alfred Kraffert; Gerhard Weiss, both of Weyhe; Rainer Spudich, Achim-Baden, all of Germany

[73] Assignee: Bruker-Franzen Analytik GmbH, Germany

[21] Appl. No.: 37,934

[22] Filed: Mar. 26, 1993

[30] Foreign Application Priority Data

Nov. 13, 1992 [DE] Germany ............... 42 38 399.4

[51] Int. Cl.6 .................. G01N 1/02; G01N 27/62; B60B 3/00; B60B 21/02
[52] U.S. Cl. .................... 73/864.71
[58] Field of Search ............... 73/864, 864.71, 864.72, 73/863

[56] References Cited

U.S. PATENT DOCUMENTS

| | | | |
|---|---|---|---|
| 3,091,967 | 6/1963 | Hardlow et al. | 73/864.71 |
| 3,430,496 | 3/1969 | Swanberg et al. | 73/864.71 |
| 3,572,128 | 3/1991 | Hemeon | 73/864.71 X |
| 3,841,973 | 10/1974 | Wilkins et al. | 73/864.71 X |
| 4,103,553 | 8/1978 | De Blasics et al. | 73/864.71 |
| 4,487,788 | 12/1984 | Scheie et al. | 73/864.72 X |
| 4,709,265 | 11/1987 | Silverman et al. | 73/864.71 |
| 4,823,084 | 4/1989 | McKinnon | 324/309 |
| 4,848,165 | 7/1989 | Bartilson et al. | 73/864.71 |
| 4,982,616 | 1/1991 | Koch et al. | 73/864.71 X |
| 5,243,865 | 9/1993 | Hsu et al. | 73/864.72 |

FOREIGN PATENT DOCUMENTS 0109633 5/1984 European Pat. Off. .

OTHER PUBLICATIONS

Jane's NBC Protection Equipment 1992-3 from Terry J. Gander pp. 131, 177–179, 181.

*Primary Examiner*—Thomas P. Noland
*Attorney, Agent, or Firm*—Bookstein & Kudirka

[57] ABSTRACT

The invention concerns a sampling device for a mobile analysis unit, in particular a mass spectrometer (13), used for the purpose of monitoring chemical substances on ground surfaces. It possesses at least one sampling wheel which revolves around an axle and which consists of a silicone tire (5) for picking up molecules of substances to be monitored and a wheel rim (6) upon which the silicone tire is fitted. The wheel rim (6) is made of metal such as stainless steel or aluminum. This means that on the one hand contamination of the silicone tire (5) by vapors from the wheel rims (6), in the course of long-term storage of the sampling wheels in airtight, closed storage containers, is prevented. On the other hand, the invention facilitates an advantageous construction of the wheel rim (6), involving the mounting of two, thin-walled rim halves (9) with rivet holes.

20 Claims, 5 Drawing Sheets

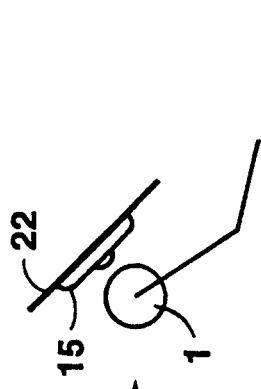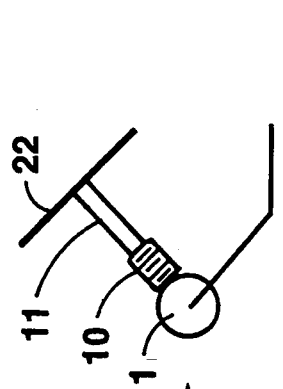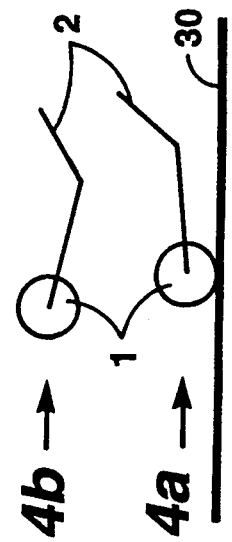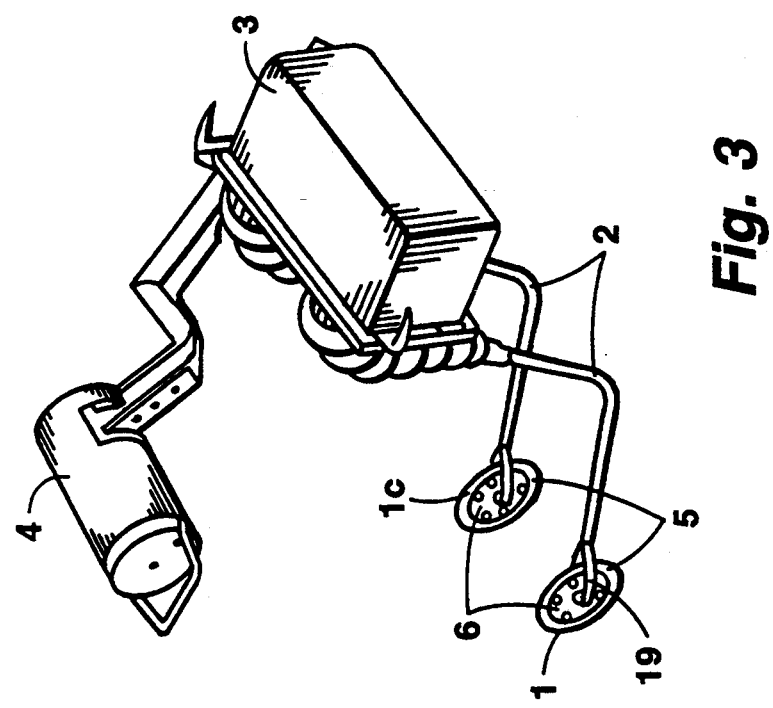

SAMPLING DEVICE COMPRISING A REVOLVABLE SAMPLING WHEEL WITH A METAL WHEEL RIM

FIELD OF THE INVENTION

This invention relates to a sampling device for a mobile analysis unit, in particular a mass spectrometer, used for the purpose of monitoring chemical substances. It possesses at least one sampling wheel which revolves around an axle and which consists of a silicone tire for picking up molecules of the substances to be monitored and a wheel rim upon which the silicone tire is fitted.

BACKGROUND OF THE INVENTION

Such a sampling device is known, for example, from the journal *Jane's NBC Protection Equipment* 1992-3, edited by Terry J. Gander, pages 131, 177-179, 181 or from the reprint out of *Kampftruppen/Kampfunterstutzungstruppen* [Combat Troops/Combat Support Troops], Issue 2/1985, E. S. Mittler & Sohn (publishers), pages 76-79.

An important area of application for the sampling device is the examination of ground contaminated by chemical substances, particularly poisons, warfare agents and the like. For this purpose an analysis unit, for example, a mass spectrometer, is installed in a vehicle encapsulated to the outside. By means of the sampling device chemical substances from outside the vehicle are fed to the analysis unit in such a way that contamination of the inside of the vehicle is impossible. In particular for the chemical sampling of the ground surface over which the vehicle travels, the sampling device can be equipped with one or more sampling wheels which consist essentially of a wheel rim rotating around an axle and a silicone tire fitted onto it. The wheels are attached to a sampling wheel arm, which pivots to bring the wheel into rotatable contact with the ground or places the wheels into various other operational positions, including in front of a sampling head projecting from the vehicle.

In order to carry out continuous measuring of ground samples from a particular stretch that has been covered while the vehicle is in operation, as a rule at least two sampling wheels with sampling wheel arms are employed in tandem operation. In the process one of the sampling wheels rolls over the ground and by means of its silicone tire picks up the substances to be analyzed, while the other sampling wheel is in a raised tracing position in front of the probe head of a sampling probe, which transfers most of the sample substances that have been collected in the silicone tires, to the analysis unit in the interior of the vehicle.

Since in the process of operation the silicone tires of the sampling wheels can in part become considerably contaminated, it is necessary to replace the sampling wheels relatively often. For this purpose as a rule several spare sampling wheels are carried along in the vehicle. These are generally stored in a closed, cylindrical container. Similar storage containers for sampling wheels are also used for long-term storage of sampling wheels outside of the vehicle.

A significant disadvantage of the previously known sampling wheels is found in the fact that until now a synthetic material was always used in the production of the wheel rim. Over a longer period of time, however, the conventional plastic rims in the gastight storage container, generally a 10-pack-can, volatilize monomers and oligomeres of the synthetic materials used for the plastic rims. During what is normally years of storage in the storage container, which typically has a gas volume of about 3-4 liters, the vapors accumulate up to a concentration of approximately 30 ppm.

The silicone tires of the sampling wheels, which must show a high degree of acceptance for chemical substances, in turn take up to a great extent the vapors from the plastic rims so that the sampling wheels are already considerably contaminated before their actual use. These chemical substances released from the plastic rims create an extremely interfering background for the measuring signal. A consequence thereof is a significant decrease to the sensitivity of the analysis unit with regard to the substances to be monitored in the course of operation.

Therefore, the present invention is to introduce a sampling device with a sampling wheel of the kind described above, for which such a contamination of the silicone tire is impossible during the long-term storage in a storage container. At the same time, however, the sampling wheel as a mass product is to be easily and inexpensively produced, and it must stand up to the stresses of operation, i.e., be able to tolerate running speeds of up to 100 km/h.

BRIEF SUMMARY OF THE INVENTION

In accordance with the invention this task is solved in a fashion which is as surprisingly simple as it is effective: The wheel rim of the sampling wheel consists of a metal such as stainless steel or aluminum. In contrast to plastic rims, no hazardous vapors, which can contaminate the silicone tires of sampling wheels, were observed in the case of metal rims, even after long-term storage of sampling wheels in a closed storage container.

For a preferred embodiment of the sampling device in accordance with this invention, the wheel rim consists of sheet metal. This makes it possible to keep the weight of the sampling wheel down while maintaining the same capacity.

In an advantageous further development of this embodiment, the wheel rim consists of two thin-walled, compressible rim disks. In this way the wheel can have a hollow design as a whole, a factor contributing to a further reduction in weight while maintaining high capacity.

In another preferred further development, each rim disk shows mounting holes in the form of rivet holes, with bead rims projecting in axial direction from the rim disks, and simple round holes. In the process of assembling two rim disks into a wheel rim, both rim disks are positioned toward one another in such a way that the bead rims of the rivet holes of one rim disk are pointed toward the other rim disk, and the rivet holes of one rim disk are positioned just opposite to the round holes of the other rim disk. The two rim disks are then simply pressed together and riveted, without necessitating additional rivet parts.

One convenient embodiment provides for an even number of mounting holes, in particular six mounting holes per rim disk. In this way for each rivet hole on the one rim disk a corresponding round hole can be provided for on the other rim disk.

The rim disks are especially easy to manufacture if the mounting holes are arranged evenly distributed in a circle around the axle. Such a symmetrical arrangement of the mounting holes also simplifies the assembly of the two rim halves into a wheel rim.

Of preference is an embodiment where the two rim disks are identical. In this way only a single kind of rim disk need be manufactured. As a result the price of the whole wheel rim is reduced, and the storage of the rim disks is simplified.

In order to completely exclude the possibility of vapors arising from the surface of the metal rims during long-term storage, one especially preferred embodiment provides a wheel rim treated by special finishing methods.

The surface of the wheel rim of one embodiment is polished, effecting a reduction of the active surface upon which any possible particles could be adhesively bonded and over a period of time revaporized.

A further possibility for surface treatment of the wheel rim is galvanization of the wheel rim. Both of these surface treatments, however, produce a more or less reflective wheel rim surface. This is particularly undesirable in military deployment of the sampling device in accordance with this invention, since during practical operation the sampling wheel is located outside the vehicle and the reflective surface could draw the attention of observers to the vehicle.

For this reason a particularly, preferred embodiment provides for a passivated wheel rim surface, preferably anodized. In this way surface treatment is attained while at the same time reflection from the wheel rim surface is prevented.

Also included within the scope of the present invention is a sampling wheel for a mobile analysis unit used for the purposes of monitoring chemical substances. It consists of a silicone tire for picking up molecules of the chemical substances to be monitored and a metal wheel rim upon which the silicone tire is fitted and which revolves around an axle.

In the following text the invention will be described and explained in more detail on the basis of the illustrated examples of embodiments. The features which may be discerned from the description and the drawing may be applied in other embodiments of the invention in any combination of individual features, alone or together with others.

The figures illustrate:

BRIEF DESCRIPTION OF THE DRAWING

FIG. 3 A three-dimensional illustration of two sampling wheels with sampling wheel arms and accompanying drive unit as well as a storage container for sampling wheels.

FIGS. 4a–4d Schematic side views of various operational positions of a sampling wheel.

DETAILED DESCRIPTION OF THE PREFERRED EMBODIMENTS

Figure 1:
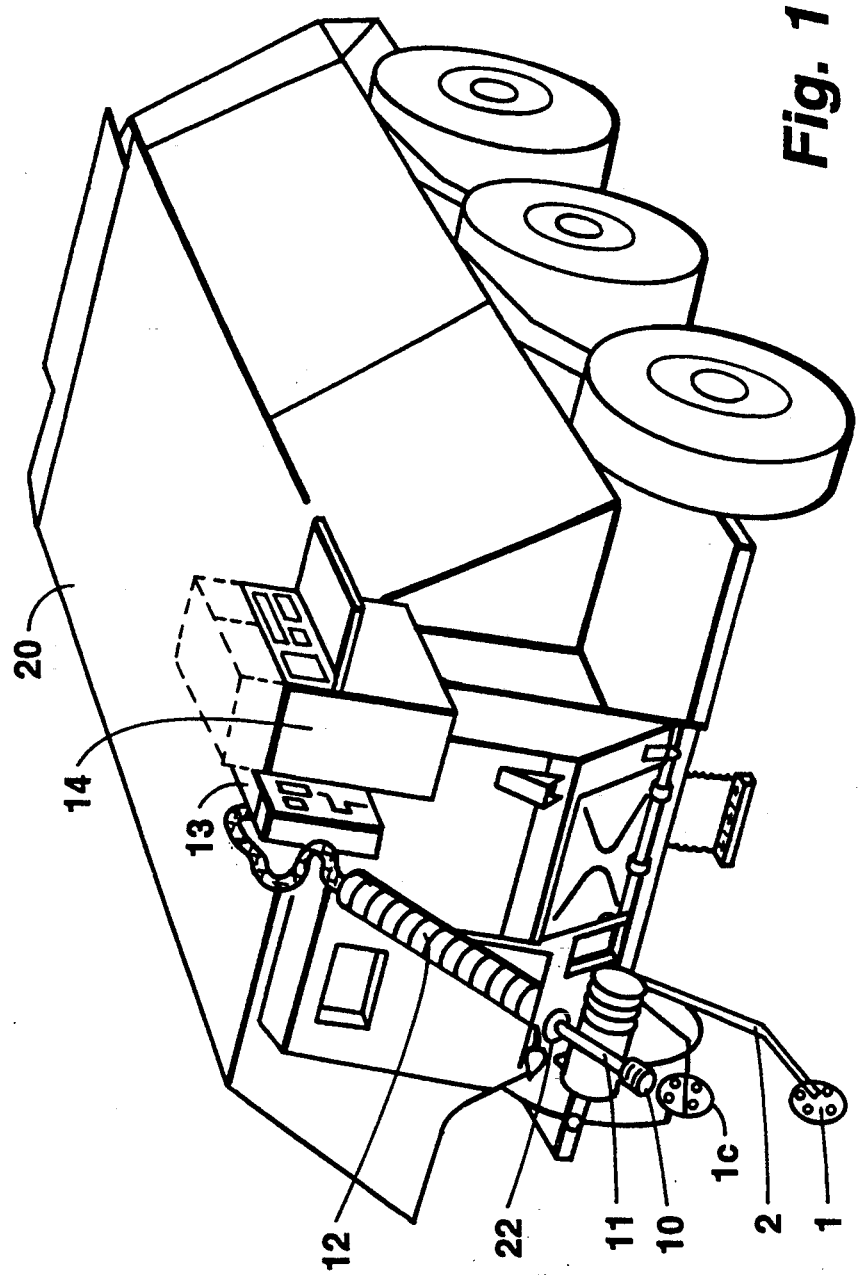
FIG. 1 A schematic rear view of a monitoring vehicle with mobile analysis unit and sampling device.

The vehicle 20 shown in FIG. 1, known as a so-called "monitoring tank" when militarily deployed, is equipped with an analysis unit for chemical substances in its rear section. The mass spectrometer 13 with the accompanying electronic analytic and display unit 14 is also visible on the drawing from the outside. On the stretch of land travelled by vehicle 20, sample substances from the ground are taken onto the silicone tire by means of a sampling wheel 1 which has been lowered onto the ground and which is attached to a sampling wheel arm. As soon as the sampling wheel 1c is brought into measuring position in front of a probe head 10, which projects from the rear section of the vehicle, the substances are fed to the mass spectrometer 13 by means of a sampling probe 11 and a feeder 12. Because two sampling wheels 1, 1c are provided for, with corresponding sampling wheel arms, in tandem operation one of the sampling wheels 1 can roll along the ground taking samples, while the other sampling wheel 1c, in measuring position, transfers the acquired sample substances to the mass spectrometer for the corresponding mass analysis. In this way continual monitoring operation is made possible during the whole trip of vehicle 20.

Figure 2:
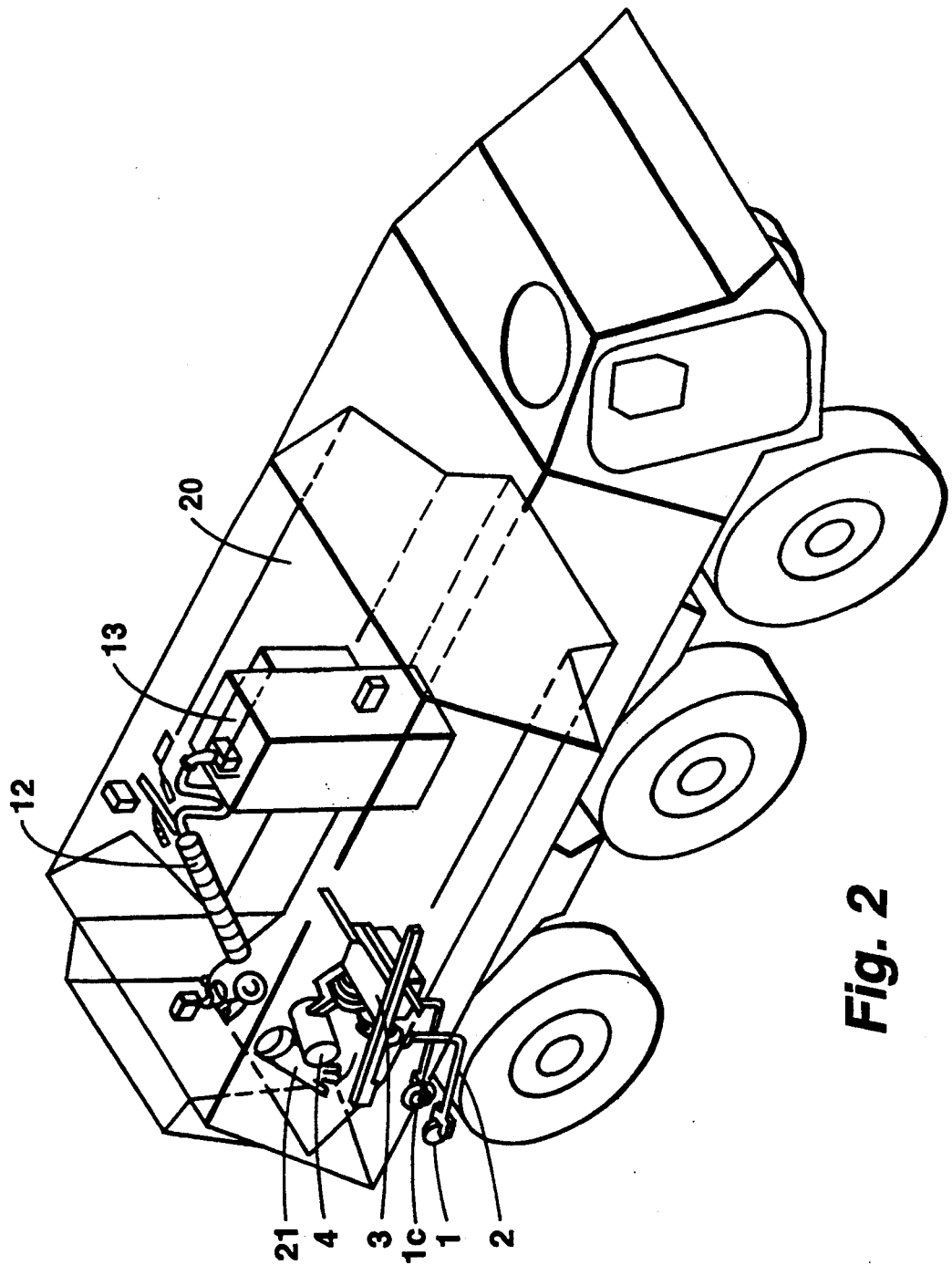
FIG. 2 A partially transparent view of a monitoring vehicle with schematic illustration of parts of the analysis unit and the sampling device.

In vehicle 20, shown in FIG. 2, it is possible to recognize again the mass spectrometer 13 with the accompanying electronic analytic and display unit as well as the feeder 12 from the sampling probe 11 which is not shown here. Furthermore, hand and arm protection is also indicated. With the help of this protection an operator in vehicle 20 can remove without contamination 4 new sampling wheels from the storage container and mount them on one of the sampling wheel arms.

In FIG. 3 the two sampling wheels 1, 1c for tandem monitoring operation are shown. The sampling wheel arms 2 can be raised and lowered via a schematically indicated drive unit. Furthermore, FIG. 3 shows clearly the structure of sampling wheels 1, 1c consisting of one wheel rim 6 and one silicone tire 5 mounted on it. Finally, FIG. 3 shows the storage container 4 for sampling wheels 1, 1c. It is provided with a lid in such a way that a contaminated sampling wheel can be exchanged for a fresh wheel while the vehicle 20 is travelling.

FIGS. 4a–4d show clearly the various operational positions for the sampling wheel 1. In FIG. 4a the sampling wheel 1 moves along in contact with the surface of the ground 30 and in the process picks up substances to be monitored by means of its silicone tire 5. FIG. 4 b, shows sampling wheel 1 in raised position above the surface of the ground 30.

In FIG. 4c the sampling wheel 1 is in measuring position in front of probe head 10 of sampling probe 11 which projects out of the vehicle rear wall.

When neither samples from the surface of the ground 30 are to be taken nor sample substances fed to the probe head 10, sampling wheel 1 is raised into the so-called transport position as shown in FIG. 4d. In this position the sampling probe 11 is pulled in through the vehicle rear wall 22 into the interior of the vehicle and covered to the outside by a probe cover 15. The drive unit 3, with which the sampling wheels 1, 1c, can be raised or lowered into positions as shown in FIG. 4a–4d is schematically represented in FIG. 3. The housing for the drive is constructed in box form. A holding mount for attachment of the storage container 4 for the sampling wheels 1, 1c as well as for the replacement membranes for the probe head 10 is fastened with screws to the side of the drive housing. The mechanism for the raising and lowering of the two sampling wheel arms is mounted within the housing.

The sampling wheel arms 2 consist essentially of bent bars at which ends the sampling wheels 1, 1c are attached to rotate over axle support 19. As a rule the sampling wheel arms are constructed of spring steel which at one end is equipped with a thread for attachment to axle support 19 and on the other end with a threaded bush, not shown in detail, for the purpose of screwing attachment to the drive 3 for the sampling arms 2.

Figure 5:
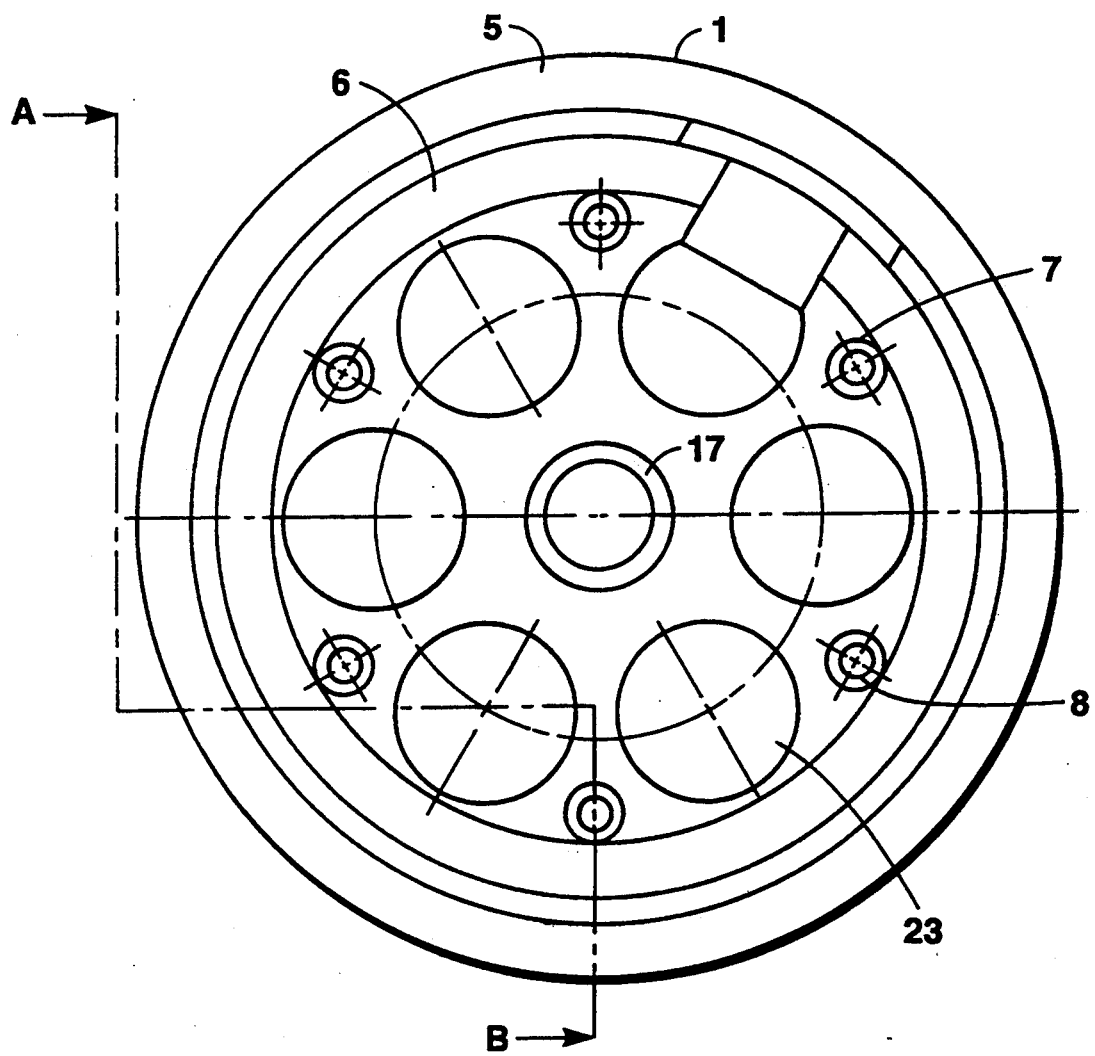
FIG. 5 A schematic side view of a sampling wheel with marked reference positions for mounting holes in the wheel rim.

FIG. 5 shows a side view of the sampling wheel 1 with silicone tire 5 and wheel rim 6. Wheel rim 6 contains round holes 7 and rivet holes 8, which serve to connect two rim disks 9 of which wheel rim 6 is constructed. In addition, the rim disks 9 contain grab holes 23, which must be large enough to allow to reach through with the hand and arm protection for the purpose of changing the sampling wheel from the interior of the vehicle. The grab holes 23 must in any case be completely burred to exclude the possibility of damage to the hand and arm protection 21 during manipulation of sampling wheel 1.

Figure 6A:
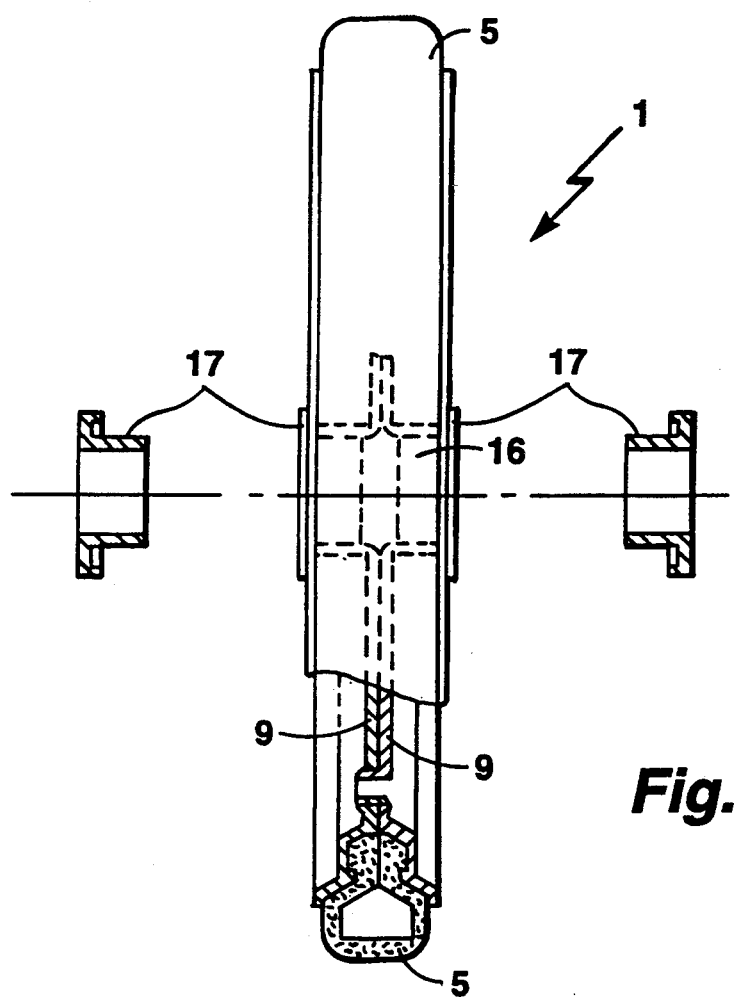
FIG. 6a A partial, front section view of a sampling wheel, consisting of two assembled rim disks as well as a silicone tire.
Figure 6B:
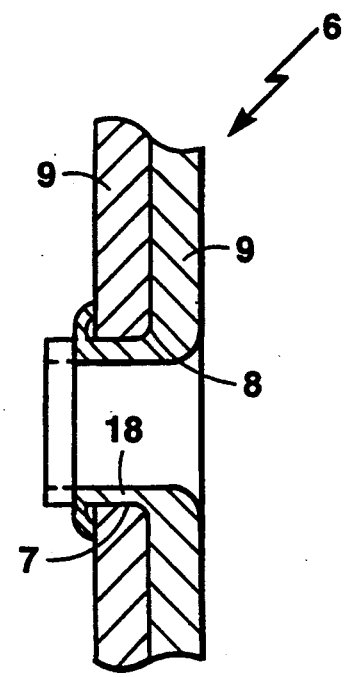
FIG. 6b A detailed section through a flanged rivet hole.

FIG. 6a is a partial front view of sampling wheel 1 showing a longitudinal section along the lines A-B in FIG. 5. It becomes clear that for the construction of the wheel rim 6, two rim disks 9 are pressed together and fastened by flanging the bead rims of the rivet holes, shown in enlarged form in FIG. 6bb, which are inserted through the round holes 7 on the other rim disk 9 opposite. The bead rim 18 is represented in FIG. 6b in both unflanged (broken lines) as well as in flanged form.

This method of attachment has the advantage that no extra rivets are needed but rather the bead rims 18 of the rivet holes 8, which are integrated into the rim disks 9, assume the function of rivets.

In the case that an even number of mounting holes are provided for (there are six mounting holes 7, 8 in the example represented in FIG. 5.), the round holes 7 and the rivet holes 8 can be arranged alternately on a rim disk 9 so that in the process of assembling two rim disks 9 into a wheel rim 6, by turning the opposite rim disk 9 on the common axle, a rivet hole 8 on the one rim disk 9 is positioned just opposite a round hole 7 on the other rim disk 9. The bead rim 18 on the rivet hole 8 can then be inserted through this opening and subsequently flanged.

Since the mounting holes 7, 8, as shown in FIG. 5, are symmetrically arranged in a reference circle distributed around the axle, it is possible to assemble two identical rim disks 9 into wheel rim 6. In this case there is no left and right side to the wheel rim, but rather only one kind of rim disk 9 need be manufactured and kept on store.

To install a pivot bearing, as a rule a Teflon bearing, head liners 17 are inserted in the axle bore hole of wheel rim 6 from both sides and screwed down or fastened in some other way.

When installed, the head liners 17 (drawn as a broken line in FIG. 6a) keep free a gap volume 16 in the middle of the axle in which dirt particles can collect so that the bearing surface of the axle bearing for sampling wheel 1 is spared of wear.

In the example shown, as the axle diameter is 14.9 mm and the bearing liners show an inside diameter of 15.1 mm, a margin of 0.2 mm remains. For this reason when the sampling wheel 1 is in a free-running state in a position raised from the surface of the ground, a rolling motion is caused which serves as a self-braking mechanism, reducing the possibly very high rotating speed of the sampling wheel 1 (the monitoring vehicle travels at speeds up to 100 km/h) prior to pressing the silicone tire 5 against the probe head 10 of the sampling probe.

The production, as described above, of a wheel rim 6 from two preferably, identical rim disks 9 can of course also be of advantage for applications other than sampling wheel 1, in particular for military vehicles.

A decisive point distinguishing the present invention lies in the fact that the wheel rim 6 is manufactured of metal instead of synthetic material as had been the case previously. This means that on the one hand contamination of sensitive silicone tires 5 by vapors from the wheel rims 6, in the course of long-term storage of the sampling wheels 1 in an airtight, closed storage container, can be prevented. On the other hand, however, the metal construction of wheel rims 6 also facilitates the aforementioned advantageous assembling possibility in which the necessary rivets are already integrated into the rim disks in the form of bead rims on rivet holes.

The calibration of the mass spectrometer 13 in the portable analysis unit for the substances ethanol, toluol, xylene and acetophenone is effected in accordance with manufacturer—s instructions, respectively, three measurements with the concentrations 0.1 ppm, 1.0 ppm and 10 ppm. From this it becomes clear that a concentration of 30 ppm due to interfering substances leads to an unacceptably high level of contamination of the sensitive silicone tires 5, such as has been observed after long-term storage of sampling wheels 1 in the storage containers when wheel rims consisting of synthetic materials were used. By using metal rims for sampling wheels an amazingly simple solution is effected, which is advantageous in other respects as well (wheel rim construction).

In order to avoid any vaporization from the wheel rims 6, the surface can also be additionally tempered. Polishing or galvanization of the wheel rim surface is conceivable. This results, however, in a tracing wheel 1 causing a stronger reflection of the light. Since this reflecting effect can be undesirable in military applications, passivation of the wheel rim surface, preferably anodization, represents as a rule a better solution.

We claim:

1. A sampling device for a mobile analysis mass spectrometer, used for the purpose of monitoring chemical substances with at least one sampling wheel revolving around an axle and comprising a silicone tire for picking up molecules of the substances to be monitored and a wheel rim upon which the silicone tire is fitted characterized in that the wheel rim consists of metal.

2. A sampling device as claimed in claim 1, characterized in that the wheel rim consists of sheet metal.

3. A sampling device as claimed in claim 1, characterized in that the wheel rim consists of two thin-walled rim disks which are pressed against each other for assembling.

4. A sampling device as claimed in claim 3, characterized in that each rim disk has mounting holes in the form of rivet holes with bead rims, projecting an axial direction from the rim disks, and round holes.

5. A sampling device as claimed in claim 4, characterized in that six mounting holes per rim are provided for.

6. A sampling device as claimed in claim 4, characterized in that the mounting holes are arranged evenly distributed in a circle around the axle.

7. A sampling device as claimed in claim 6, characterized in that the rim disks are identical.

8. A sampling device as claimed in claim 1, characterized in that the surface of the wheel rim is tempered.

9. A sampling device as claimed in claim 1, characterized in that the surface of the wheel rim is polished.

10. A sampling device as claimed in claim 1, characterized in that the surface of the wheel rim is galvanized.

11. A sampling device as claimed in claim 1, characterized in that the surface of the wheel rim is anodized.

12. A sampling wheel for a mobile analysis mass spectrometer for the purpose of monitoring chemical substances, comprising a silicone tire for picking up molecules of the substances to be monitored and a wheel rim upon which the silicone tire is fitted and which can be revolvably mounted to an axle, characterized in that the wheel rim is constructed of one of stainless steel and aluminum.

13. A sampling wheel according to claim 12, wherein the wheel rim consists of sheet metal.

14. A sampling wheel according to claim 12, wherein the wheel rim consists of two thin-walled rim disks which are pressed against each other for assembling.

15. A sampling wheel according to claim 14, wherein each rim disk has mounting holes in the form of rivet holes with bead rims, projecting in axial direction from the rim disks, and round holes.

16. A sampling wheel according to claim 15, wherein an even number of mounting holes, are provided for, and wherein the mounting holes are arranged evenly distributed in a circle around the axle.

17. A sampling wheel according to claim 16, wherein the rim disks are identical.

18. A sampling wheel according to claim 12, wherein the surface of the wheel rim is polished.

19. A sampling wheel according to claim 12, wherein the surface of the wheel rim is anodized.

20. A sampling wheel for a mobile analysis mass spectrometer for the purpose of monitoring chemical substances, comprising a silicone tire for picking up molecules of the substances to be monitored and a wheel rim upon which the silicone tire is fitted and which can be revolvably mounted to an axle, characterized in that the wheel rim is constructed of sheet metal, that the wheel rim is constructed of two thin-walled rim disks which are pressed against each other for assembling, that each rim disk has mounting holes in the form of rivet holes with bead rims, projecting in an axial direction from the rim disks, and round holes, that an even number of mounting holes per rim disk, are provided for, that the mounting holes are arranged evenly distributed in a circle around the axle, that the rim disks are identical, that the surface of the wheel rim is hardened, and that the surface of the wheel rim is passivated.

* * * * *